United States Patent
Ramos (10) Patent No.: US 12,064,373 B2
(45) Date of Patent: *Aug. 20, 2024

(54) APPARATUS AND METHODS OF USING AN INTRA-VAGINAL FLUID COLLECTION DEVICE

(71) Applicant: Charise D. Ramos, Zephyrhills, FL (US)

(72) Inventor: Charise D. Ramos, Zephyrhills, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/341,648

(22) Filed: Jun. 26, 2023

(65) Prior Publication Data

US 2023/0329896 A1 Oct. 19, 2023

Related U.S. Application Data

(63) Continuation of application No. 17/187,584, filed on Feb. 26, 2021, now Pat. No. 11,723,789.

(60) Provisional application No. 62/983,083, filed on Feb. 28, 2020.

(51) Int. Cl.
*A61F 5/455* (2006.01)
*A61F 5/44* (2006.01)

(52) U.S. Cl.
CPC .......... *A61F 5/4553* (2013.01); *A61F 5/4407* (2013.01); *A61F 5/4404* (2013.01)

(58) Field of Classification Search
CPC ...... A61F 5/4553; A61F 5/4404; A61F 5/455; A61F 5/4407
See application file for complete search history.

(56) References Cited

U.S. PATENT DOCUMENTS

| 300,770 | A | * | 6/1884 | Farr | A61F 5/455 604/331 |
| 1,743,733 | A | * | 1/1930 | Spardel | A61F 5/4553 604/331 |
| 2,182,702 | A | * | 12/1939 | Previn | A61F 5/4553 604/331 |

(Continued)

FOREIGN PATENT DOCUMENTS

| GB | 2 413 286 A | 10/2005 | |
| GB | 2413286 A | * 10/2005 | A61F 5/455 |

OTHER PUBLICATIONS

Final Office Action on U.S. Appl. No. 17/187,584 DTD Dec. 5, 2022.

(Continued)

*Primary Examiner* — Guy K Townsend
(74) *Attorney, Agent, or Firm* — Foley & Lardner LLP (57) ABSTRACT

Arrangements described herein relate to a device for collecting intravaginal fluid. The device is defined by a hollow collector and a flexible fluid collection bag, wherein the device is configured such that when inserted into the vagina, the hollow collector forms a seal with the inner walls of the vagina, while the fluid collection bag extends outside the body. By allowing fluid to collect outside the body rather than inside the, the device is permitted to be narrow in diameter (such as, for example, the diameter of a tampon), to increase user comfort. Flaps at the opening of the hollow collector may be used to seal fluid within the device when it is extracted from the body.

20 Claims, 12 Drawing Sheets

(56) References Cited

U.S. PATENT DOCUMENTS

| | | | | | |
|---|---|---|---|---|---|
| 3,102,541 | A * | 9/1963 | Adams | .................. | A61F 5/4553 604/15 |
| 3,128,767 | A * | 4/1964 | Nolan | ...................... | A61F 6/08 604/330 |
| 3,626,942 | A * | 12/1971 | Waldron | .................... | A61F 6/08 604/330 |
| 3,958,561 | A * | 5/1976 | Bucalo | ............ | A61B 5/150213 600/575 |
| 4,085,755 | A * | 4/1978 | Burrage | .................... | A61F 5/44 604/350 |
| 4,232,673 | A * | 11/1980 | Bucalo | .............. | A61B 10/0045 604/328 |
| 4,381,771 | A * | 5/1983 | Gabbay | ...................... | A61F 6/08 128/836 |
| 4,534,766 | A * | 8/1985 | Steer | ..................... | A61G 7/0503 604/350 |
| 4,848,363 | A * | 7/1989 | Cattanach | .............. | A61F 5/4553 128/834 |
| 4,961,436 | A * | 10/1990 | Koch | ........................ | A61F 6/08 128/834 |
| 5,295,984 | A * | 3/1994 | Contente | ............... | A61F 5/4553 604/327 |
| 5,498,252 | A * | 3/1996 | Silber | ..................... | A61F 13/34 604/330 |
| 5,827,248 | A * | 10/1998 | Crawford | .............. | A61F 5/4553 604/328 |
| 6,168,609 | B1 * | 1/2001 | Kamen | ................. | A61F 5/4553 600/573 |
| 6,241,846 | B1 * | 6/2001 | Contente | ............... | B29C 66/114 156/379 |
| 6,264,638 | B1 * | 7/2001 | Contente | ............. | A61M 31/002 604/285 |
| 7,875,010 | B2 * | 1/2011 | Frazier | .................... | A61F 5/455 604/347 |
| 8,454,493 | B2 * | 6/2013 | La Vean | ..................... | A61F 6/08 600/33 |
| 10,016,308 | B2 * | 7/2018 | Knox | ................ | A61F 13/00085 |
| 10,188,545 | B2 * | 1/2019 | Conti | ......................... | A61F 6/12 |
| 10,357,395 | B2 * | 7/2019 | Miller | .................... | A61F 5/4404 |
| 11,219,548 | B2 * | 1/2022 | Conti | ........................ | A61F 6/12 |
| 11,291,535 | B2 * | 4/2022 | Conti | .................... | A61F 2/0095 |
| 11,723,789 | B2 * | 8/2023 | Ramos | ................... | A61F 5/4553 604/330 |
| 2002/0143303 | A1 * | 10/2002 | Intravartolo | .............. | A61F 6/08 604/385.18 |
| 2008/0077097 | A1 * | 3/2008 | Chambers | ............. | A61F 5/4553 604/330 |
| 2008/0200888 | A1 * | 8/2008 | Gooch | .................. | A61F 5/4553 604/330 |
| 2010/0312204 | A1 * | 12/2010 | Sheu | ...................... | A61F 5/4408 604/330 |
| 2013/0110060 | A1 * | 5/2013 | Shihata | .................. | A61F 5/4553 604/330 |
| 2015/0164680 | A1 * | 6/2015 | Chen | ................... | A61F 13/8405 604/359 |
| 2016/0030020 | A1 | 2/2016 | Buurstede et al. | | |
| 2016/0278988 | A1 * | 9/2016 | Knox | .................... | A61F 15/005 |
| 2017/0189222 | A1 * | 7/2017 | Lin | ....................... | A61F 5/4553 |
| 2017/0360594 | A1 * | 12/2017 | Park | ........................ | A61F 5/449 |
| 2019/0083296 | A1 * | 3/2019 | Miller | ................... | A61F 5/4553 |
| 2020/0022835 | A1 * | 1/2020 | Lloveras Macià | .... | A61F 5/4404 |
| 2021/0267788 | A1 * | 9/2021 | Ramos | ................... | A61F 5/4553 |
| 2023/0329896 | A1 * | 10/2023 | Ramos | ................... | A61F 5/4407 |

OTHER PUBLICATIONS

International Preliminary Report on Patentability for corresponding PCT Application PCT/US2021/020102, issued by the International Searching Authority, dated Sep. 9, 2022, 6 pages.

International Search Report and Written Opinion for PCT/US2021/020102 dated May 19, 2021.

Non-Final Office Action on U.S. Appl. No. 17/187,584 DTD Jun. 24, 2022.

Notice of Allowance on U.S. Appl. No. 17/187,584 DTD Mar. 27, 2023.

* cited by examiner

APPARATUS AND METHODS OF USING AN INTRA-VAGINAL FLUID COLLECTION DEVICE

CROSS-REFERENCE TO RELATED APPLICATIONS AND CLAIM OF PRIORITY

This application is a Continuation Application of U.S. patent application Ser. No. 17/187,584, filed Feb. 26, 2021, which claims the benefit of U.S. Provisional Application No. 62,983,083, filed Feb. 28, 2020, the content of which are fully incorporated herein by reference in their entireties.

BACKGROUND

There are several reasons to need and use an intra-vaginal fluid collection device; for instance, to address menses, endometriosis, post-pregnancy uterine shedding, and/or the need to collect valuable samples for medical testing. There are several methods of intra-vaginal fluid collection in the market, but each has its own shortcomings. For example, a tampon has limits on how much fluid it can collect (generally, around 3-12 mL). Tampons also require changing every 8 hours, and come with the risk of Toxic Shock Syndrome (TSS). Tampons also do not collect fluid in a manner where a doctor could conveniently run tests on the fluid. Another example, the sanity pad, has similar shortcomings, including limits on how much it can collect (generally, around 5-15 mL) and inability for a doctor to run tests on the fluid. Pads additionally require users to sit in their own blood, which is uncomfortable. Another option is the menstrual cup. Cups can generally hold up to 25 mL of fluid. However, removal of the cup often results in spilling the contents of the cup as the suction between the cup and the vaginal walls is broken—this process is messy and loses valuable fluid for doctors to test. The cup also requires insertion of the hand into the vagina to insert and remove the cup, exposing the vagina to any bacteria or viruses on the hands. Because menstrual cups are designed to hold a substantial amount of fluid within the body, they have a certain minimum width requirement that many users find uncomfortable.

To address the shortcomings of the available fluid collection methods, the present invention has several benefits: the device can collect more fluid (with capacity at minimum of 100 mL); it is made of a medical grade silicone to prevent TSS risk; and the user can open and close the device, allowing for easy, clean removal and allowing for full collection of fluid for testing. Further, the device can be inserted or removed without contacting the vagina with the user's hand. Finally, by allowing fluid to collect outside the body, the width of the device can be relatively narrow in comparison to a menstrual cup, and thus more comfortable for most users.

In some arrangements, an intra-vaginal fluid collection device includes a hollow outer membrane having an upper section and a lower section. The device includes a first opening at the proximal end of the upper section, such that the first opening has a plurality of flexible flaps to close the upper section. The device includes a hollow inner collector having an upper portion and a lower portion, wherein the upper portion has a substantially circular opening at its proximal end that opens into a hollow cup, and wherein the lower portion of the inner collector is attached to the cup opposite from the cup's opening. The device may be constructed such that the inner collector may be placed within the outer membrane, with the upper section of the outer membrane enveloping the upper portion of the inner collector, and the lower section of the outer membrane surrounding the lower portion of the inner collector. When combined in this manner, the device has a combined upper part and a combined lower part.

SUMMARY

In some arrangements, an intra-vaginal fluid collection device includes a hollow outer membrane having an upper section and a lower section. The device includes a first opening at the proximal end of the upper section, such that the first opening has a plurality of flexible flaps to close the upper section. The device includes a hollow inner collector having an upper portion and a lower portion, wherein the upper portion has a substantially circular opening at its proximal end that opens into a hollow cup, and wherein the lower portion of the inner collector is attached to the cup opposite from the cup's opening. The device may be constructed such that the inner collector may be placed within the outer membrane, with the upper section of the outer membrane enveloping the upper portion of the inner collector, and the lower section of the outer membrane surrounding the lower portion of the inner collector. When combined in this manner, the device has a combined upper part and a combined lower part.

In some arrangements, the combined upper part is inserted into a vagina of a user while the combined lower part extends from within the vagina to outside of the vagina. The inner collector may be manipulated by the user such that the opening of the inner collector protrudes out of the opening of the outer membrane, allowing fluid to be collected into the opening of the inner collector. In some arrangements, the hollow inner collector can function without the hollow outer membrane. In some arrangements, the outer membrane may also collect fluid simultaneously with the inner collector. Where the outer membrane has flaps at its proximal opening, these may seal in the inner collector before use, and then again after fluid collection to help seal the fluid within the device.

In another arrangement, a method of using an intra-vaginal fluid collection device includes inserting the device in a vaginal canal by pushing the device proximally. The method includes holding a grip portion of an outer membrane to hold the device in place. The method includes manipulating an inner collector proximally up through a plurality of flexible flaps of the outer membrane. The method includes leaving the device in place to collect fluid. The method includes pulling the inner collector distally to position the inner collector back inside the outer membrane. The method includes removing the device from the vaginal canal by pulling the device distally. A removal mechanism such as a tab, ring or grip on the lower section of the outer member may assist with removal from the vagina after use.

It should be noted that as used herein, terms like "upper" and "lower" do not limit the device to any particular spatial orientation, but rather merely distinguish one side of the device from another.

BRIEF DESCRIPTION OF THE FIGURES

Features and aspects of arrangements will become apparent from the following description and the accompanying example arrangements shown in the drawings, which are briefly described below.

DETAILED DESCRIPTION

The detailed description set forth below in connection with the appended drawings is intended as a description of various configurations and is not intended to represent the only configurations in which the concepts described herein may be practiced. The detailed description includes specific details for providing a thorough understanding of various concepts. However, it will be apparent to those skilled in the art that these concepts may be practiced without these specific details. In some instances, well-known structures and components are shown in block diagram form in order to avoid obscuring such concepts.

In the following description of various arrangements, reference is made to the accompanying drawings which form a part hereof and in which are shown, by way of illustration, specific arrangements in which the arrangements may be practiced. It is to be understood that other arrangements may be utilized, and structural changes may be made without departing from the scope of the various arrangements disclosed in the present disclosure.

Figure 1A:
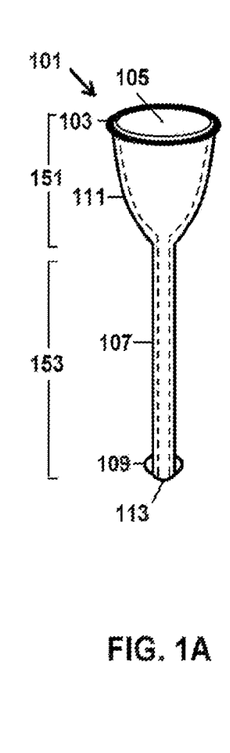
FIG. 1A is a side view of an embodiment of the inner collector.

Referring to FIG. 1A, an embodiment of an inner collector 101 is shown with dashed lines indicating its walls. The inner collector 101 has an upper portion 151 comprised of a hollow cup 111 with an opening 105 that has a protruding circumferential lip 103. The cup 111 may be constructed of a silicone material or similar that is generally sufficiently stiff to retain its shape when constricted within the user's body, though also capable of being flexed when squeezed firmly by a human hand. In some embodiments, the cup may be sufficiently rigid to not flex under human hand pressure. The lower portion 153 of the inner collector 101 is comprised of a hollow tube 107 with an opening 113 and a rim 109. The tube 107 may be made from a silicone material that is sufficiently thick and/or rigid to ensure that the hollow cavity within the tube 107 does not collapse or become pinched during use, while also being flexible enough to comfortably bend within the user's body when in use. The rim 109 is intended to provide a gripping point for manipulation of the inner collector, as will be described further herein. The rim 109 should be large enough to enable manipulation of the inner collector by the user, while also being small enough to not cause discomfort to the user while within the body.

Referring to FIG. 1A, an embodiment of an inner collector 101 is shown with dashed lines indicating its walls. The inner collector 101 has an upper portion 151 comprised of a hollow cup 111 with an opening 105 that has a protruding circumferential lip 103. The cup 111 may be constructed of a silicone material or similar that is generally sufficiently stiff to retain its shape when constricted within the user's body, though also capable of being flexed when squeezed firmly by a human hand. In some embodiments, the cup may be sufficiently rigid to not flex under human hand pressure. The lower portion 153 of the inner collector 101 is comprised of a hollow tube 107 with an opening 113 and a rim 109. The tube 107 may be made from a silicone material that is sufficiently thick and/or rigid to ensure that the hollow cavity within the tube 107 does not collapse or become pinched during use, while also being flexible enough to comfortably bend within the user's body when in use. The rim 109 is intended to provide a gripping point for manipulation of the inner collector, as will be described further herein. The rim 109 should be large enough to enable elation of the inner collector by the user, while also being small enough to not cause discomfort to the user while within the body.

Other embodiments of the inner collector are possible, and some will be shown herein in later figures. For example, in some embodiments, the cup need not drain into a tube, and the lower portion of the inner collector might be used solely as a handle for manipulating the position of the inner collector when inside the body. In other embodiments, the inner collector need not have a lower portion at all, and instead comprise only a hollow cup.

The shape and size of the cup need not be limited to that shown in the figures. Functionally, the diameter of the cup is intended to be wide enough to form a seal within the vaginal canal so as to collect fluid while minimizing the amount of fluid that can pass by it along the vaginal walls, while the cup diameter should also be small enough to cause minimum discomfort to the user. In many instances, the diameter of the cup may be similar to that of a standard tampon. This is notably narrower than the diameter of most menstrual cups currently on the market, which necessarily must be larger so as to accommodate more fluid collection, whereas the devices and methods disclosed herein contemplate fluid collection to partially occur outside the body. Different sizes of cups may be offered to accommodate different users. The length and shape of the cups may vary as well, with the goal again being to create an opening in the vagina for effective fluid collection, while minimizing diameter so as to maximize comfort.

The cup may be semi-rigid, so that it is capable of deforming somewhat under the pressure of the vaginal walls, while also rigid enough to generally maintain its shape during use and allow fluid to pass through the cup. Different sizes may be offered (for example, Small, Medium, and Large) to accommodate different users, and may range in diameter from approximately 10 mm to approximately 40 mm. In all instances, the cup diameter may be such as is minimally required to create a good seal with the vaginal walls, whereby almost all fluid flowing out of the vagina will flow into the cup rather than travel around the rim of the cup along the vaginal walls (recognizing that because of the dynamic shape and movement of the vaginal walls, a perfect seal would be inherently difficult to obtain). Some degree of trial and error may be needed for a given user to find the diameter size that works best for them, trying different diameter sizes until they arrive at one that is sufficiently narrow to be comfortable and preferable to a menstrual cup, while sufficiently wide to minimize leakage during expected use, accounting for how active the user may intend to be while the device is inserted.

Figure 1B:
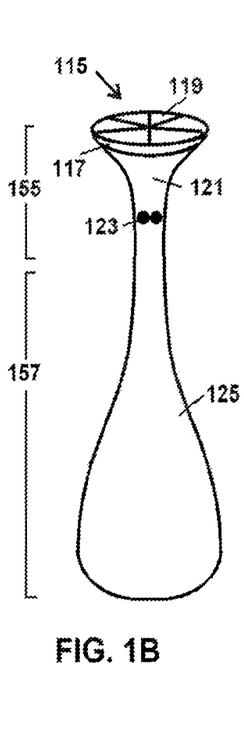
FIG. 1B is a side view of an embodiment of the outer membrane.

Referring now to FIG. 1B, and embodiment of the outer membrane shown. FIG. 1B is an external view of the outer membrane rather than a cutaway. Here, an outer membrane 115 is comprised of an upper section 155 and a lower section 157. At the proximal and of the upper section 155 is a rim 117 that supports a series of flexible flaps 119 that cover the opening of the upper section. The rim 117 may be constructed of a semi-rigid material such as silicone that is sufficiently thick and/or rigid to hold the flaps 119 in their relative orientation to each other to keep the opening of the upper section closed. The balance of the upper section 155 comprises a flexible elastic material 121 (such as, for example, latex or equivalent) that constricts inwardly toward the axis of the outer membrane.

Dimples 123 are hemispherical indentations in the upper section that ultimately act as suction cups when the device is in use inside the body. These dimples 123 may be a few millimeters in diameter, and may be positioned at various points on the surface of the upper section of the outer membrane. The elastic material 121 may be thick enough throughout to support the dimples 123, or may be thicker only where the dimples 123 are located. As will be shown in later drawings, because the dimples 123 rest atop the elastic material 121, when the elastic material 121 is stretched away from the axis of the outer membrane, the dimples 123 are stretched away from one another.

The lower section 157 of the outer membrane 115 comprises a flexible collection bag 125. The collection bag 125 may be made of a thin elastic material such as latex (or equivalent). The purpose of the collection bag 125 is to collect bodily fluids. It is intended that the collection bag 125 extend from and protrude from the vagina when the device is in use so as to allow fluid volume to partially build up outside the body, rather than inside the body, and thereby advantageously reduce the need to store fluid inside the body (as many other fluid collection devices do).

Figure 1C:
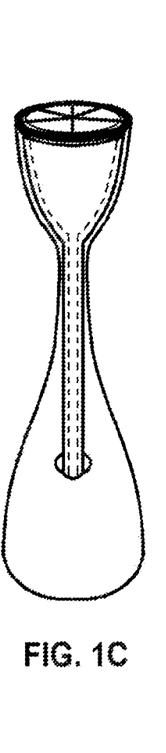
FIG. 1C is a side cut-away view of an embodiment of the device with the inner collector from FIG. 1A placed inside of the outer membrane from FIG. 1B.

Referring now to FIG. 1C, a cutaway side view is shown of the outer membrane 115 with inner collector 101 placed within it to form a combined device 159. Flaps 119 cover opening 105 of the inner collector 101, and thereby create a seal. The cup 111 pushes outward on the elastic material 121, stretching it away from the axis of the outer membrane 115. The tube 107 runs down into the lower section 157 of the outer membrane 115, with the rim 109 and opening 113 located within the hollow space of the collection bag 125.

Figure 1D:
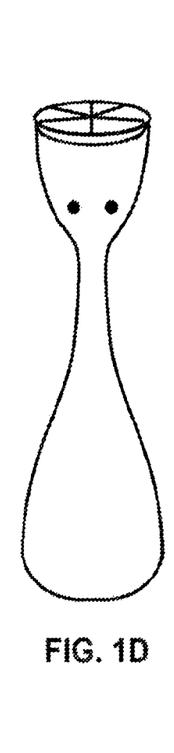
FIG. 1D is a side view of the embodiment shown in FIG. 1C showing what the device looks like on its exterior when the inner collector is inside of the outer membrane.

Referring now to FIG. 1D, and exterior side view is shown of the combined device 159 that was depicted in FIG. 1C. As can be seen, the dimples 123 have been stretched apart from one another by the presence of the cup 111. In this state, the elastic material 121 of the upper section 155 of the outer membrane 115 is squeezing inwardly on the exterior of the cup 111, though not enough to cause the cup 111 to protrude through the flaps 119.

Figure 1E:
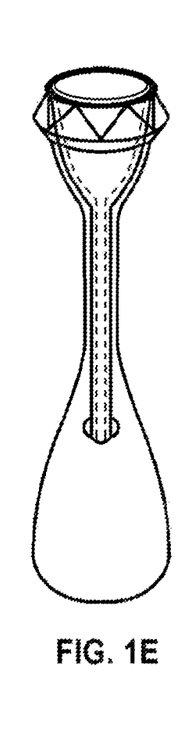
FIG. 1E is a side cut-away view of the embodiment from FIG. 1C, but with the upper portion of the inner collector protruding through the opening of the upper section of the outer membrane.

Referring now to FIG. 1E, a cutaway side view is shown of the inner collector 101 protruding up through the flaps 119 of the outer membrane 115, thereby exposing the opening 105 of the cup 111 to the surrounding environment, and enabling fluid collection through the opening 105. The inner collector 101 may be pushed upwards through the flaps 119 by the user manipulating the inner collector 101 with their fingers through the outer membrane 115, such as by squeezing the outer membrane around the lower portion of the cup 111, or by engaging the rim 109 of the inner collector 101 through the collection bag 125, and using the rim 109 to push upwardly on the inner collector 101. Note that the tube 107 should be sufficiently stiff and/or rigid to allow such force to be applied without simply buckling the tube 107.

Referring now to FIG. 1E, a cutaway side view is shown of the inner collector 101 protruding up through the flaps 119 of the outer membrane 115, thereby exposing the opening 105 of the cup 111 to the surrounding environment, and enabling fluid collection through the opening 105. The inner collector 101 may be pushed upwards through the flaps 119 by the user manipulating the inner collector 101 with their fingers through the outer membrane 115, such as by squeezing the outer membrane around the lower portion of the cup 111, or by engaging the rim 109 of the inner collector 101 through the collection bag 125, and using the rim 109 to push upwardly on the inner collector 101. Note that the tube 107 should be sufficiently sick and or rigid to allow such force to be applied without simply buckling the tube 107.

As can be seen in FIG. 1E, the circumferential lip 103 may rest atop the tips of the flaps 119, helping to hold the inner collector extended away from the body of the outer membrane. Note also that in this configuration, fluid may enter into the outer membrane through the gaps between the flaps 119, and then flow into the collection bag 125. As is apparent from this depiction, the diameter of the rim 117 of the outer membrane should match the diameter of the opening that is desired to be created within the body when the device is in use, and should be sufficiently wide to press against walls of the vaginal cavity surrounding it so as to create a seal and minimize any body fluid flowing past the outside of the rim 117, and then out of the body. Note that the cup 111 acts to reinforce the rim 117 against inward pressure by the surrounding body cavity.

In some embodiments, the segmented flaps 119 may be replaced with a continuous elastic membrane (made of latex or similar material) with a small central opening, such that the cup 111 may be pushed up through it, causing the elastic membrane to widen to allow the cup 111 to pass, and then constricting around the cup 111 just under the rim 117. In such an embodiment, fluid flow would be largely limited to the cup 111, rather than the flow that might otherwise be allowed through openings between the flaps 119.

Figure 1F:
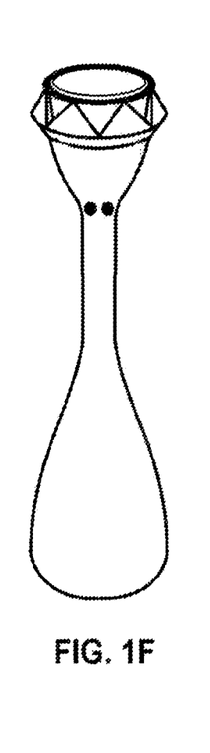
FIG. 1F is a side view of the embodiment shown in FIG. 1E showing what the device looks like on its exterior when in the state shown in FIG. 1E.

Referring now to FIG. 1F, an exterior side view is shown of the combined inner collector and outer membrane that was depicted in FIG. 1E. As can be seen, because the cup 111 has shifted upwards, the elastic material 121 between the dimples 123 has contracted, bringing the dimples 123 closer together, and also acting to help hold the cup 111 in position Various steps may also be taken to prevent the inner collector 101 from sliding upward out of the outer membrane 115 to an undesired degree. For example, the elastic material 121 may be limited to comprising a band encircling the upper section 155 of the outer membrane. That way, the band will act to help push the cup 111 into its desired deployed position, but once the cup 111 reaches its desired deployed position, the band would contract, and the rest of the material above the band that comprises the upper section 155 of the outer membrane 115 would apply minimal pressure to the cup 111. Alternatively or additionally, the upper part of the lower section 157 might comprise a semi-rigid tube, and the tube 107 of the inner collector might have a structure on its outer surface that is sufficiently wide to be incapable of fitting through the outer membrane's semi-rigid tube, thereby limiting the degree of upward travel of the inner collector 101 relative to the outer membrane 115. Such a structure might also be combined with the rim 109. In other embodiments, direct linkage between the inner collector 101 and the outer membrane 115 may be introduced to ensure that the inner collector 101 does not protrude out of the outer membrane 115 to an unwanted degree.

In a mode of use, the combined device 159 is inserted into the vagina in its sealed state as depicted in FIGS. 1C and 1D. A user can then manipulate the inner collector 101 through the outer membrane 115 to cause the inner collector 101 to protrude up through the flaps 119 as shown in FIGS. 1E and 1F. Such manipulation can be performed (either with the user's fingers, or with a comparable instrument) on the rim 109 of the inner collector 101 through the collection bag 125, using the rim 109 to push the internal collector 101 up relative to the outer membrane. It may be helpful in performing the manipulation to simultaneously hold the collection bag 125, or pull gently down on it, so as to facilitate the movement of the inner collector and outer membrane relative to one another.

The device 159 is then left in place within the vagina to collect fluid, with the collection bag 125 mostly outside of the body so that fluid can collect there rather than inside the body. The device 159 may collect fluid through the opening 105 of the internal collector, flowing into the cup 111 and down through the tube 107 into the collection bag 125. In some embodiments, the tube 107 may be made long enough to also extend into the collection bag 125 outside the body. Fluid may also collect between the flaps 119 and into the outer membrane 115, flowing around the internal collector 101 and into the collection bag 125.

Continuing in discussing a mode of use of the device 159, when it is desired to remove the device 159, the user can manipulate the inner collector 101 to cause it to retract back into the outer membrane 115. Such manipulation can be accomplished with the user's fingers (or a comparable instrument) by pulling downwardly on the rim 109. Once the inner collector 101 is retracted, the flaps 119 will elastically seal off the top of the device 159, and then the device 159 call be pulled out of the vagina by pulling on the collection bag 125.

Referring now to FIGS. 2-5, a vaginal fluid collection device 100 is illustrated according to various arrangements. As shown, the device 100 includes an outer membrane 102 and an inner collector 104. The outer membrane 102 has an upper section 106 and a lower section 108. The upper section 106 and the lower section 108 are coupled with a first tapered portion 110. The upper section 106 is a frustoconical shape which narrows toward the distal end of the upper section 106, toward the first tapered portion 110. The lower section 108 is a compliant member (e.g., a balloon, expandable bag, etc.) coupled to the first tapered portion 110, such that the lower section 108 expands out from the first tapered portion 110. The upper section 106 is a flexible and elastic material, thus accommodating to vagina walls. The lower section 108 is a flexible and elastic material, thus configured to receive a variable volume of fluid. As such, the upper section 106 is a thicker and more rigid material than the lower section 108. The upper section 106 has a first opening 112 at the proximal end of the upper section 106. The first opening 112 is designed to be opened and closed upon manipulation by the user. The first opening 112 include flexible flaps 114 to aid in the sealing of the device 100 during insertion and removal. For instance, the flexible flaps are configured with a plurality of sealing holes 114a which create a suctioning effect when inserted in the user.

The inner collector 104 has an upper portion 116 and a lower portion 118. The upper portion 116 and the lower portion 118 are coupled with a second tapered portion 120. The upper portion 116 is a frustoconical shape which narrows toward the distal end of the upper portion 116, toward the second tapered portion 120. The lower portion 118 is a compliant member (e.g., a balloon, flexible bag/sack.) coupled to the second tapered portion 120, such that the lower portion 118 expands out from the second tapered portion 120. The upper portion 116 is a rigid material (i.e., a cup), such that the fluid is captured by the upper portion 116. The upper portion 116 may be a biodegradable plant based plastic. The lower portion 118 is a flexible and elastic material, thus accommodating the receipt of a relatively unknown volume of fluid. The upper portion 116 has a second opening 122. The second opening 122 is generally circular and is designed to remain open. The second opening 122 has rounded edges to reduce discomfort for the user.

Figure 2:
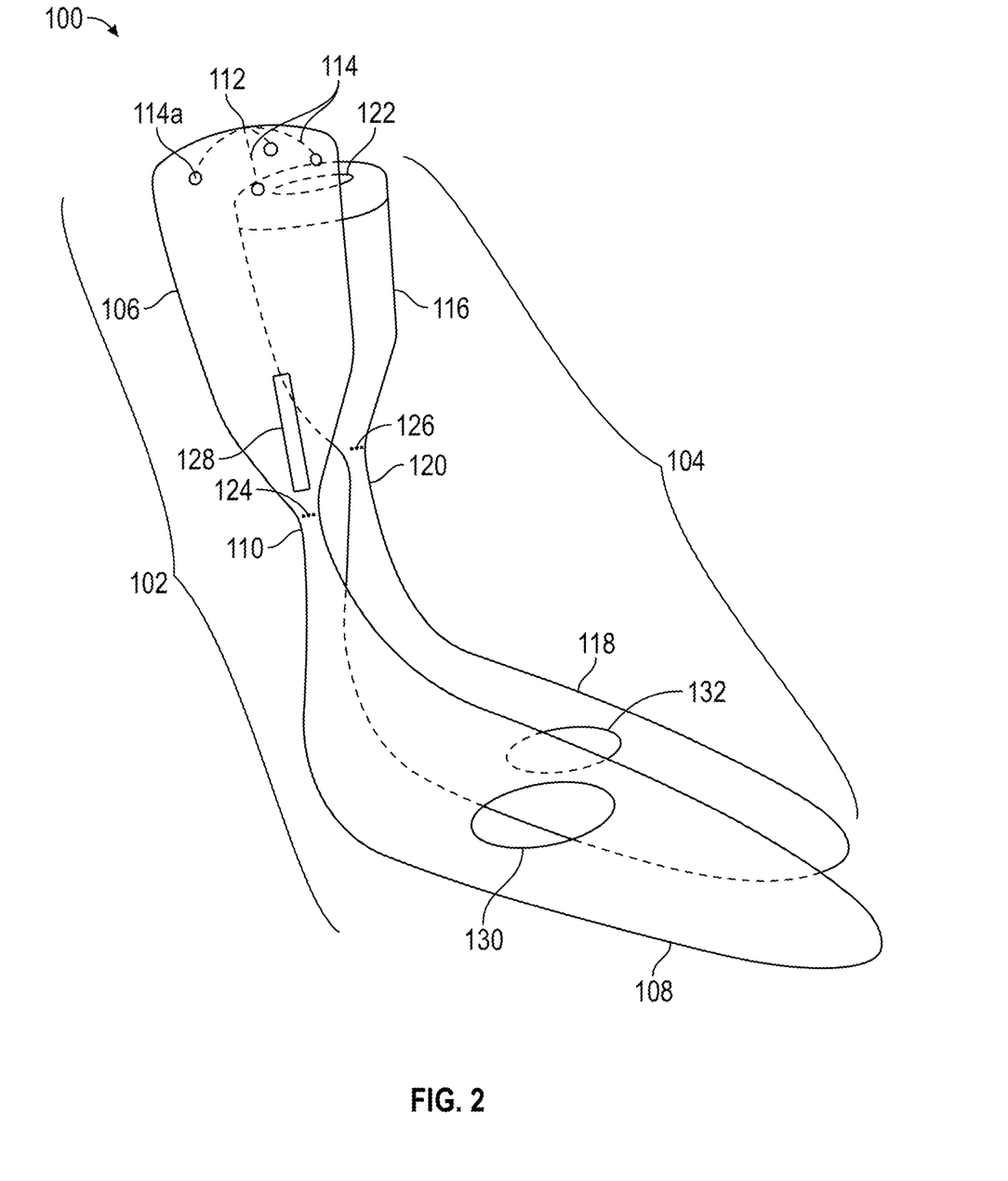
FIG. 2 is a perspective view of a fluid collection device, according to an exemplary embodiment.
Figure 3:
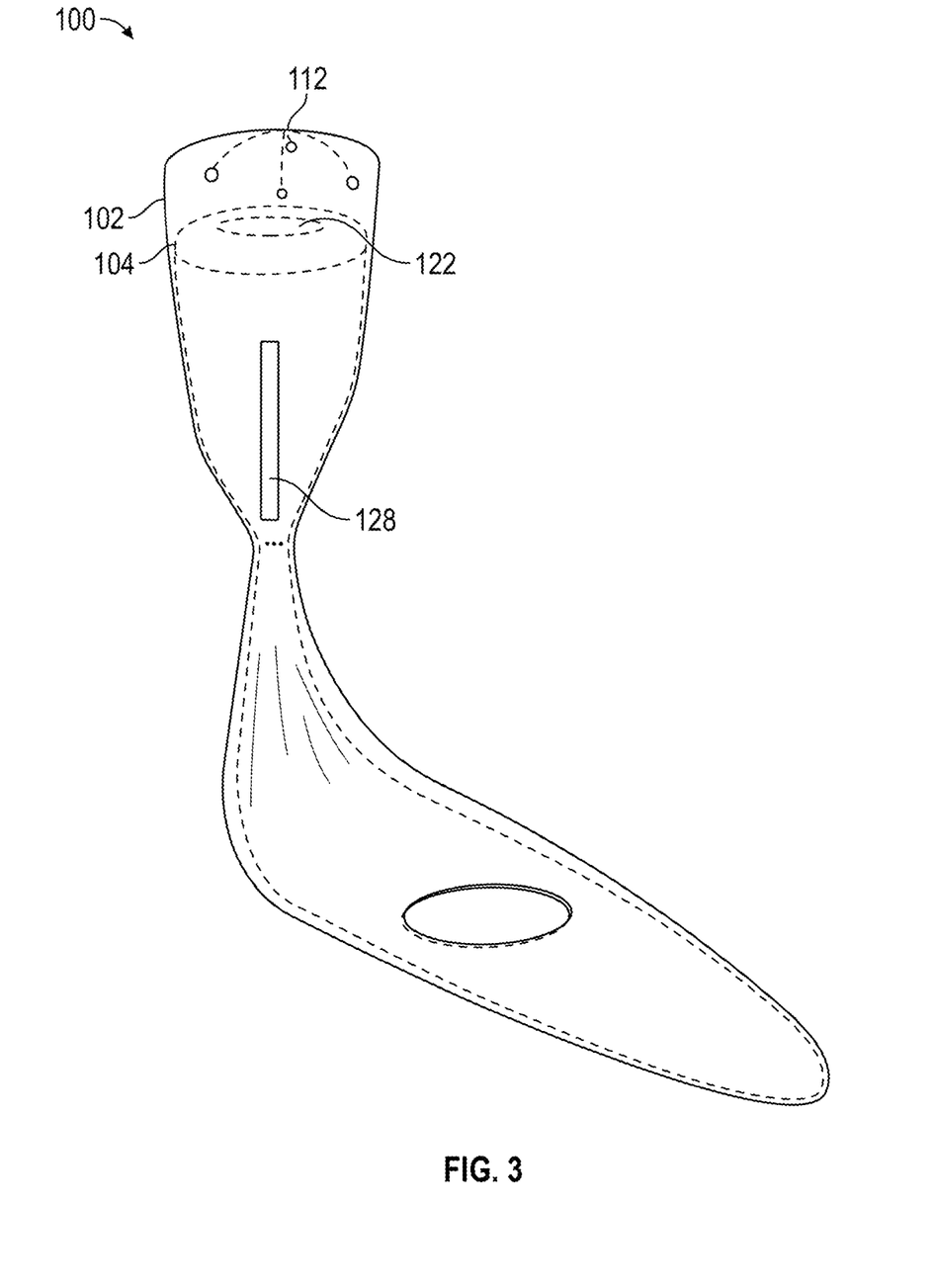
FIG. 3 is a perspective view of the fluid collection device of FIG. 1.
Figure 4A:
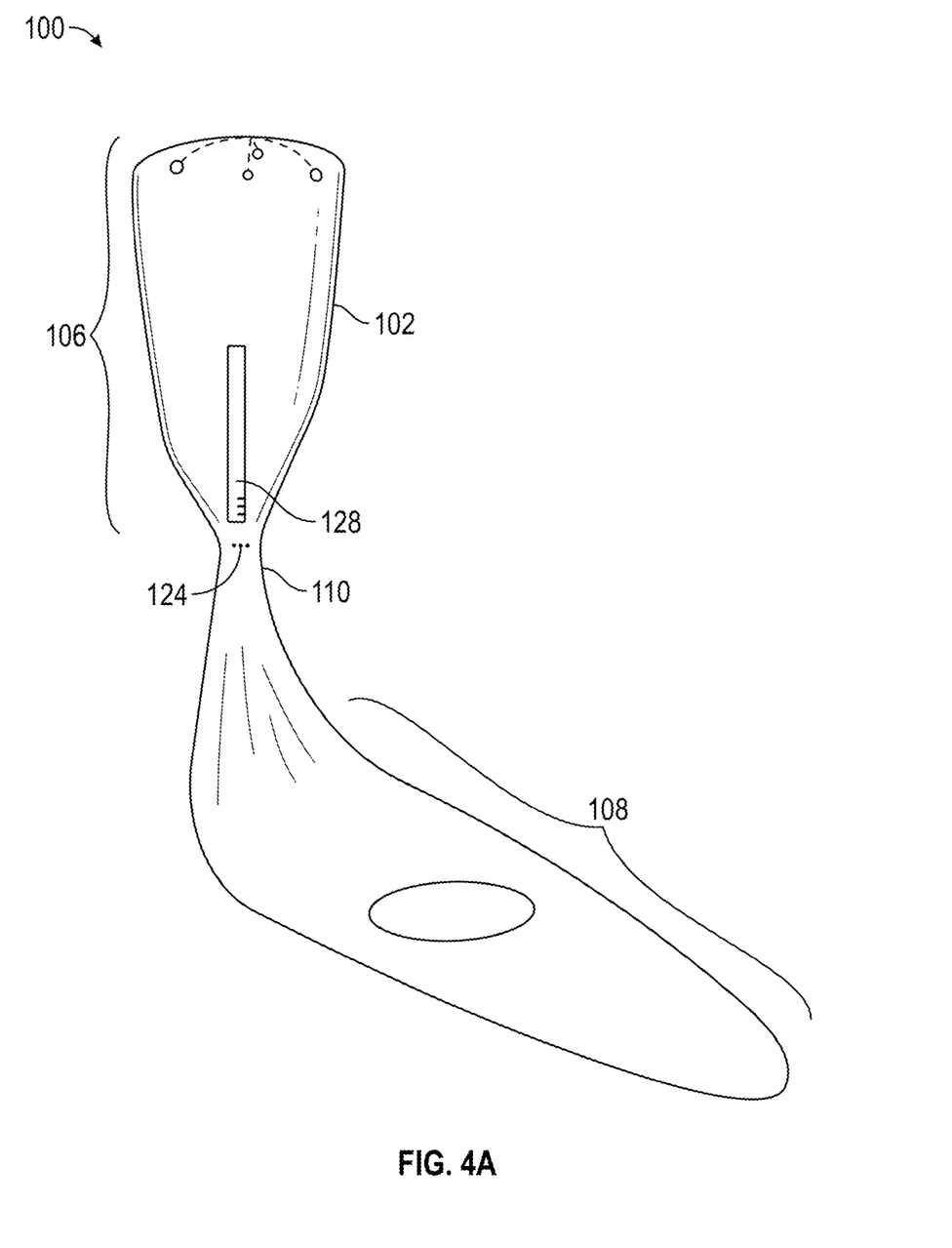
FIG. 4A is a perspective view of the fluid collection device of FIG. 1.
Figure 4B:
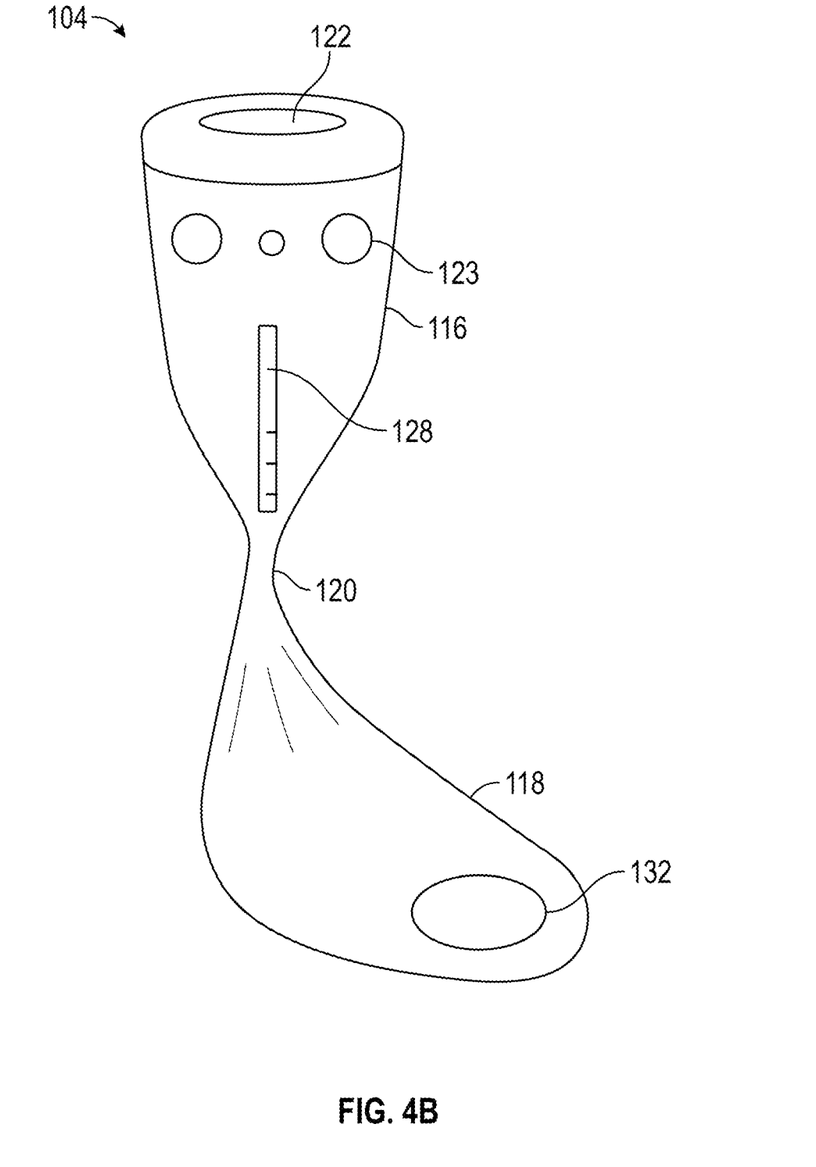
FIG. 4B is a perspective view of the fluid collection device of FIG. 1.
Figure 5:
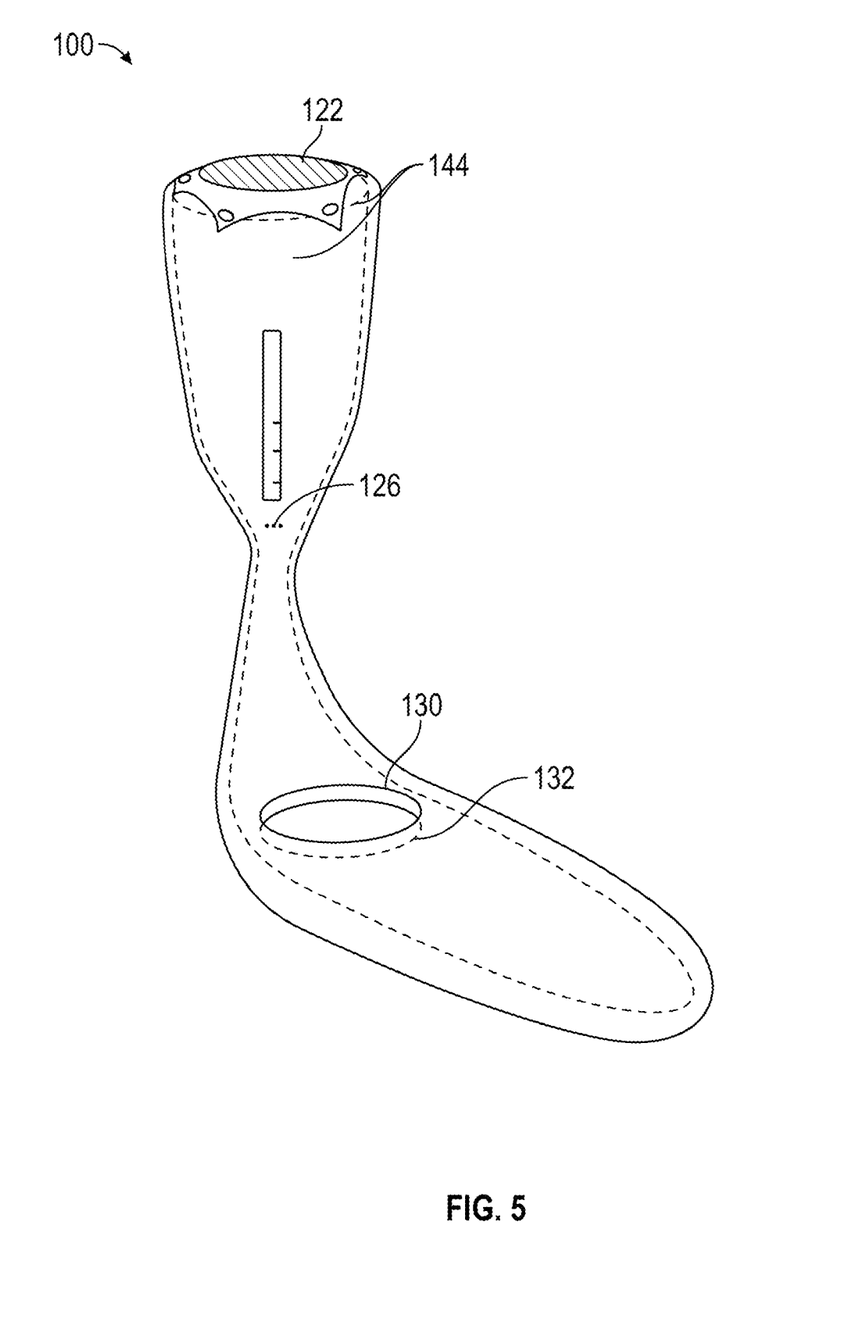
FIG. 5 is a perspective view of the fluid collection device of FIG. 1.

As can be seen in FIG. 3-5, the outer membrane 102 is an outer cover to the inner collector 104 (the outer membrane 102 appears translucent in FIG. 3 for illustration purposes only). The upper section 106 and the lower section 108 correspond with the upper portion 116 and the lower portion 118. The inner collector 104 is sized and shaped to fit within the outer membrane 102. As such, the outer membrane 102 is operatively coupled to an inner collector 104. The outer membrane 102 is provided for leak protection, over flow, and anti-spill guard. However, the inner collector 104 may be used independently (e.g., exclusively, without the outer membrane 102). In some arrangements, the first and second tapered portions 110, 120 have the first and second grip indentations 124, 126, respectively, that can assist with holding and manipulating the device 100. For instance, while pushing the inner collector 104 into an open position, as seen in FIG. 5, or pulling the inner collector 104 back into a closed position, as seen in FIGS. 2-4, the user can grasp the inner collector 104 and the outer membrane 102 at the first and second grip indentations 124, 126 to prevent slipping. To manipulate the device 100 into an open position, the user can hold the outer membrane 102 in place with one hand at the first tapered portion 110, using the first grip indentations 124 for traction. The user can feel through the outer membrane 102, due to its thin, rubber-like material, to the inner collector 104 to position their fingers at the second grip indentations 126, located near distal end of the upper portion. The user can then push the upper portion 116 out of the upper section 106 by squeezing and sliding their fingers proximally. As the upper portion 116 is pushed out through the first opening 112, the flexible flaps 114 open, thus creating suction with the plurality of sealing holes 114a and the vaginal walls. The device 100 may remain in this open configuration for the duration of the fluid collection needs. Fluid enters the second opening 122 while the device 100 is actively open in the vaginal canal. Fluid is directed through the second tapered portion 120 and into the lower portion 118 where it is captured until emptied. To remove, the user lines their fingers again at the first grip indentations 124 to hold the outer membrane 102 in place and feels through the material to locate the second grip indentations 126 to move the upper portion 116 distally, thus releasing the seal and allows the flexible flaps 114 to close.

In some arrangements, the outer membrane 102 and inner collector 104 have a transparent panel 128 such that a user can view the contents of the inner collector 104. This can help the user determine whether it is time to empty the contents. In some arrangements, the outer membrane 102 and inner collector 104 have a first removal mechanism 130 and a second removal mechanism 132 in the lower section 108 and the lower portion 118 to facilitate the removal of the entire device 100. As shown in FIGS. 2-5 and 8, the first and second removal mechanisms 130. 132 may be configured within the lower section 108 and the lower portion 118 (e.g., a hole, ring). In some embodiments, the first and second removal mechanisms 130, 132 may comprise external handles, additional gripping indentations, a pull cord, etc. In some embodiments, the lower portion 118 does not includes a removal mechanism. The removal mechanism does not affect the manipulation of the device between an open and a closed configuration due to the elasticity of the second tapered portion 120 (i.e., when the upper portion 116 is pushed out, the second tapered portion 120 stretches with, and the entire inner collector 104 does not need to shift within the outer membrane 102). Once the upper portion 116 is positioned back inside the upper section 106, as described herein, the entire device may be pulled distally via the first and second removal mechanisms 130, 132 to remove the device 100 from the user.

Figure 6:
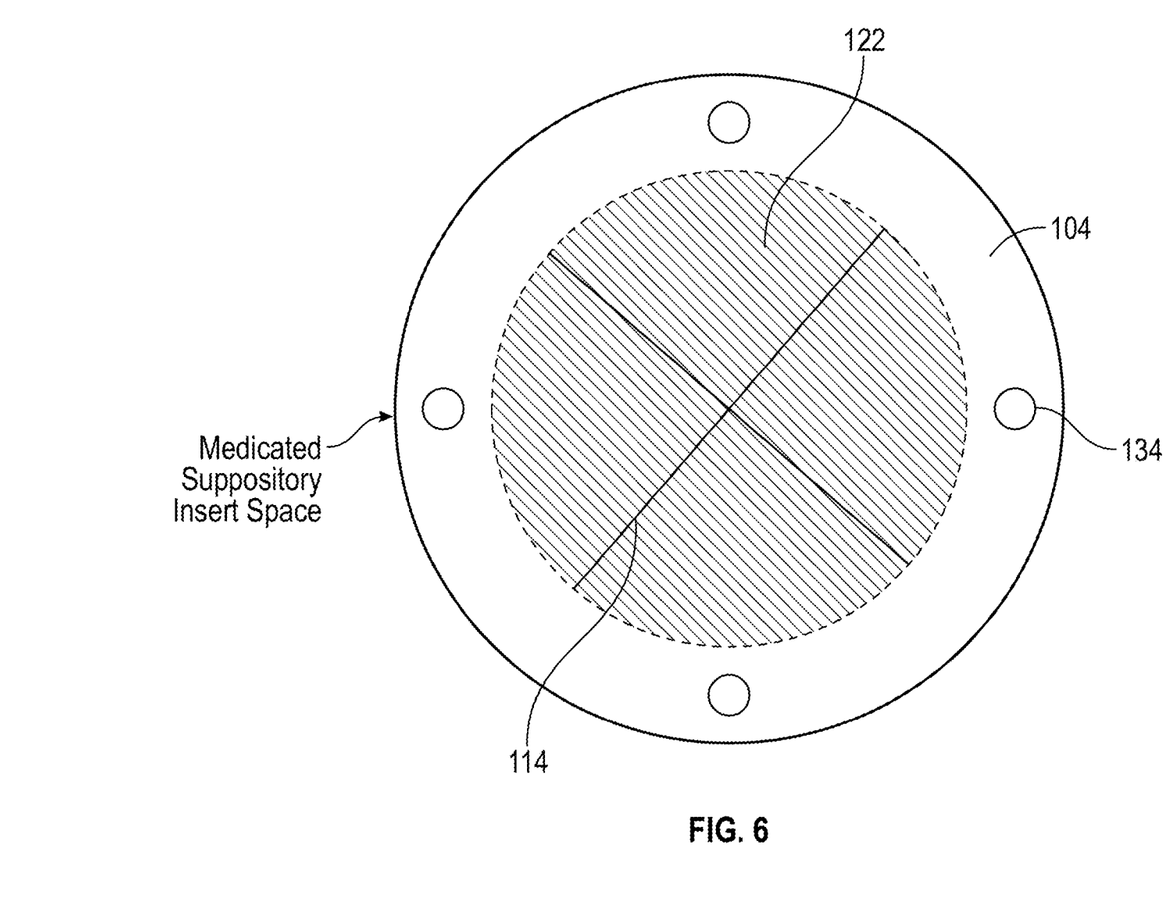
FIG. 6 is a top view of a fluid collection device, according to an exemplary embodiment.

Referring now to FIG. 6, in some arrangements, the inner collector 104 has at least one pocket 134 for suppositories. The at least one pocket 134 may be positioned on the top edge of the inner collector 104 (i.e., where the "cup" rounds over into the second opening 122). The at least one pocket 134 is used to insert medicated pills. As such, when the device 100 is in use, the medicated pills can release medication to the area.

Figure 7:
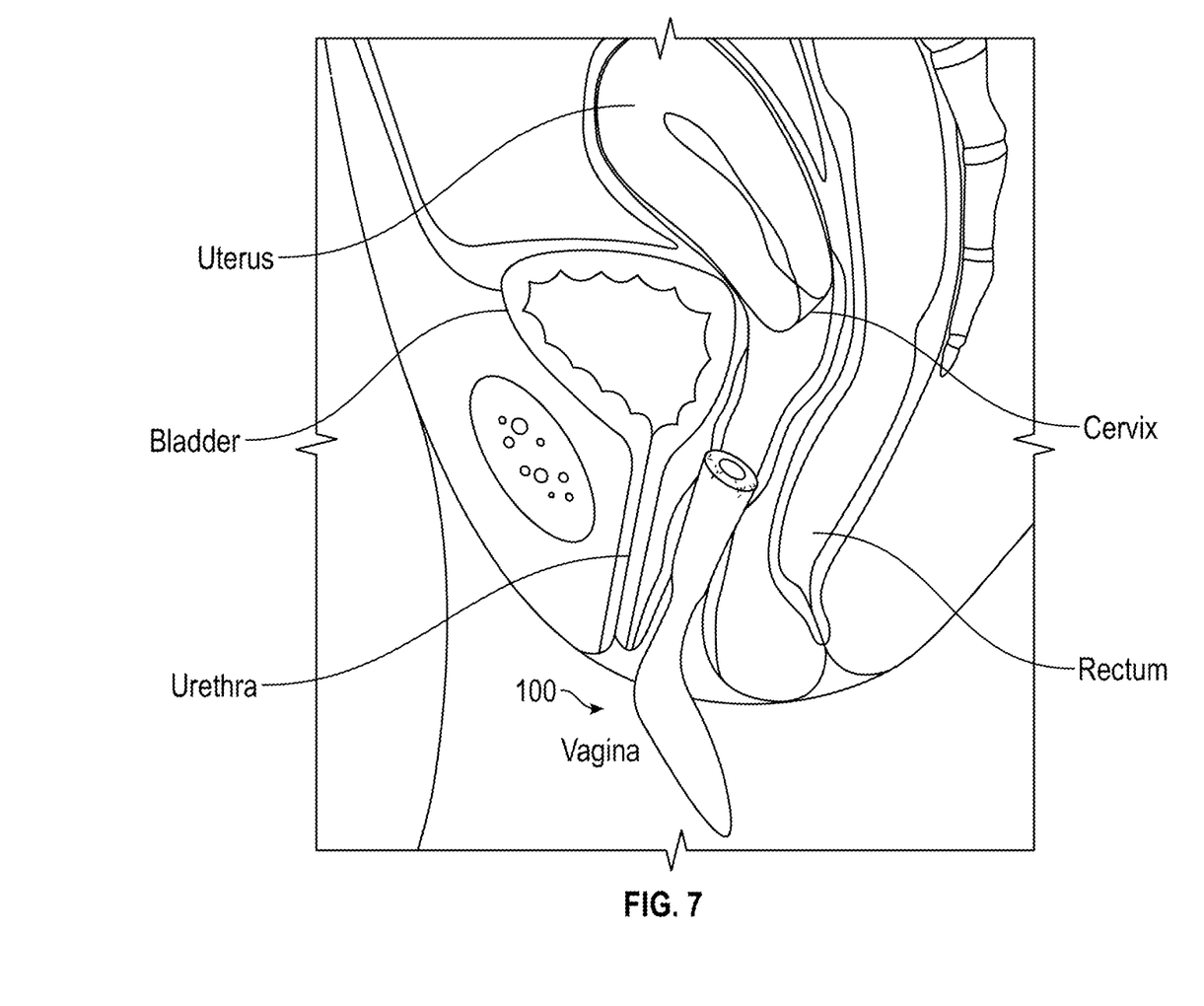
FIG. 7 is a side perspective view of the device inserted within a vagina.

FIG. 7 shows a side view of the device 100 inserted within a vagina. The upper section 106 and the upper portion 116 are disposed within the vagina, and the lower section 108 and the lower portions 118 remain outside of the vagina. In some embodiments, the device 100 is used in conjunction with, but not interfering with, a catheter. The device 100 can be available in different sizes. The outer membrane 102 and inner collector 104 are designed to prevent skin contact with the fluid.

Figure 8:
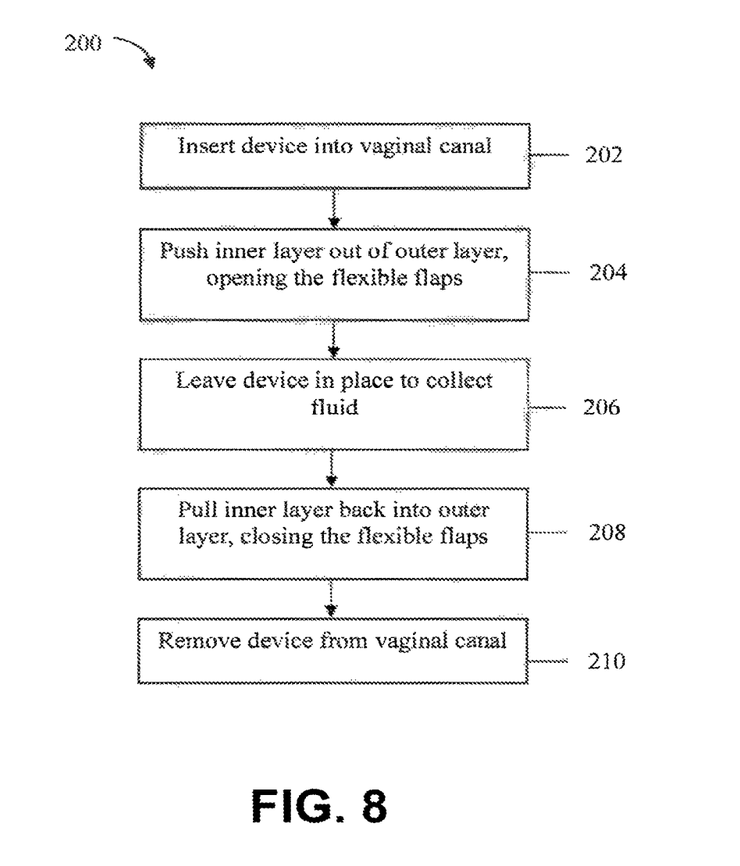
FIG. 8 is a flow chart illustrating a method of using a fluid collection device, according to an exemplary embodiment.

FIG. 8 illustrates a method 200 of using the device 100. At step 202, the device 100 is inserted into the vaginal canal (i.e., similar to inserting a cup or tampon) by pushing the entire device 100 proximally through the vagina. The user then holds the first grip indentations 124 and pushes, via the second grip indentations 126, the inner collector 104 proximally up through the flexible flaps 114 of the outer membrane 102 at step 204. At step 206, the user leaves the device 100 in place to collect fluid. To remove, the user gently pulls the inner collector 104 distally into a closed position at step 208 (i.e., positioning the inner collector 104 back inside the outer membrane 102 via the first and second gripping portions 124, 126 and the first and second removal mechanisms 130, 132). The flexible flaps 114 aid in sealing the device 100 when the device is in a close position, thus preventing the fluid from spilling when the device 100 is removed. Lastly, at step 210, the entire device 100 is removed.

Figures 9A, 9B:
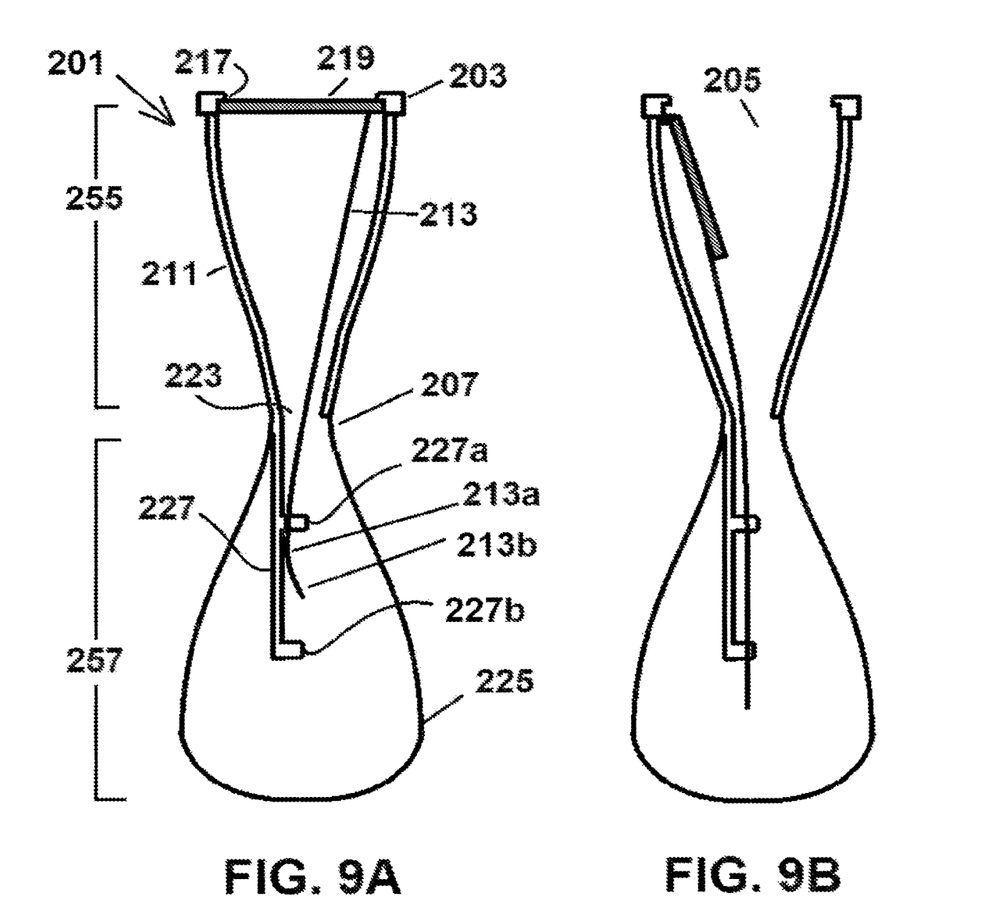
FIG. 9A is a side cross-sectional view of another embodiment of a fluid collection device.
FIG. 9B is another side cross-sectional view of the device shown in FIG. 9A.

Referring now to FIG. 9A, a side cross-section view of an embodiment of a fluid collection device 201 is shown that does not have a separate inner collector and outer membrane. Rather, device 201 has an upper portion that comprises a hollow semi-rigid cone 211 that may be made of a material such a silicone, being made thick and/or rigid enough to generally hold its shape against the pressure inside the vagina when inserted. The cone 211 has an upper rim 203 that also may be made of a material such as silicone such that it can maintain a ring shape when within the vaginal canal to maintain a roughly circular opening 205. The diameter of rim 203 should be minimally wide enough to create an opening to collect fluids with an adequate seal between the rim 203 and the vaginal walls, yet as narrow as possible within that constraint so as to cause minimal discomfort to the user. Different sizes may be offered to accommodate different users. A sealing flap 219 (which also may be made of a soft semi-rigid material like silicone) fits under the rim and is attached to the rim 203 at flexible joint 217, which acts like a hinge.

The cone 211 has a lower opening 223 that empties into the lower portion of the device 201, which comprises a flexible collection bag 225, which may be made of a thin elastic material like latex or equivalent mounted to the cone at junction 207. Extending downward into the collection bag 225 from cone 211 is a semi-rigid thin tab 227 with two or more projections 227a and 227b. The tab 227 may be made of semi-rigid silicone material or equivalent that can flexibly bend while also being able to hold the projections 227a and 227b at a distance from cone 211.

Attached to the underside of sealing flap 219 is a semi-rigid band 213 which can bend, but is stiff enough to not collapse on itself when placed in compression during the use described herein. Band 213 extends down through hollow cone 211 into collection bag 225 where band 213 terminates in a tab 213b with one or more openings 213a that are shaped to engage either of projections 227a and 227b, and may "snap" in place on those projections in the manner of loose button, to be released by pulling tab 213b away from tab 227. To maintain sealing flap 219 closed, the band 213 is positioned to press it up against rim 203, with opening 213a engaged with projection 227a. To maintain sealing flap 219 in the open position shown in FIG. 9B, tab 213b may be used to decouple opening 213a from projection 227a, and then tab 213b may be used to press and snap opening 213a onto projection 227b, which action will pull downwardly on band 213 and sealing flap 219, causing sealing flap 219 to pivot about flexible joint 217.

In a manner of use, device 201 may be inserted into the vagina with the sealing flap 219 in the open position so as to collect fluid. Collection bag 225 extends out of the vagina and allows fluid to collect outside the body. When fluid collection is complete, the user may manipulate tab 213b of band 213 through the flexible collection bag so as to disengage opening 213a from projection 227b and snap opening 213a onto projection 227a, thereby moving the band 213 upward and applying force to close sealing flap 219 against the underside of rim 203. The device 201 may then be pulled out of the vagina by the user by pulling on collection bag 225, or any attachment or handle placed on collection bag 225. Collection bag 225 may be constructed with a "doughnut-shaped" opening so as to create a pull tab that a finger can fit through to pull.

Figure 10A:
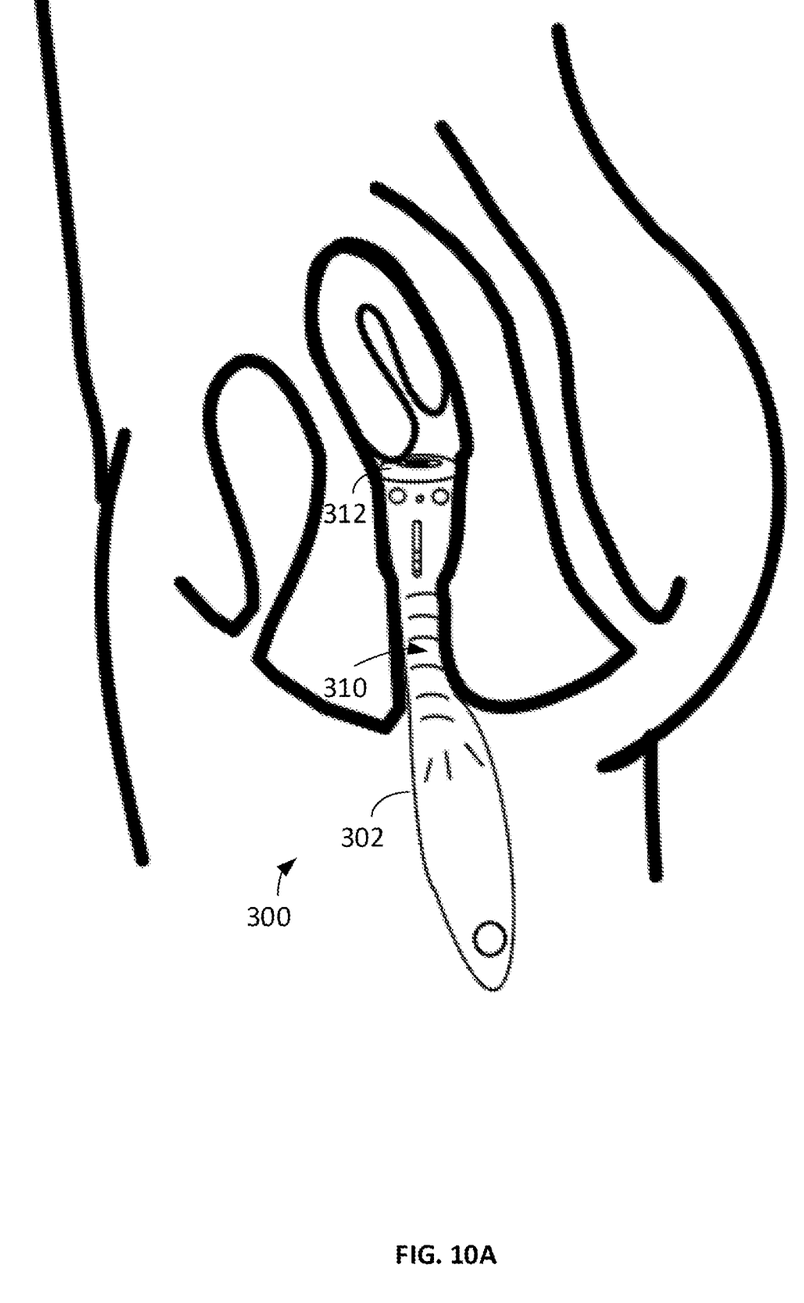
FIG. 10A is a schematic view of another embodiment of a fluid collection device inserted within a vagina.
Figure 10B:
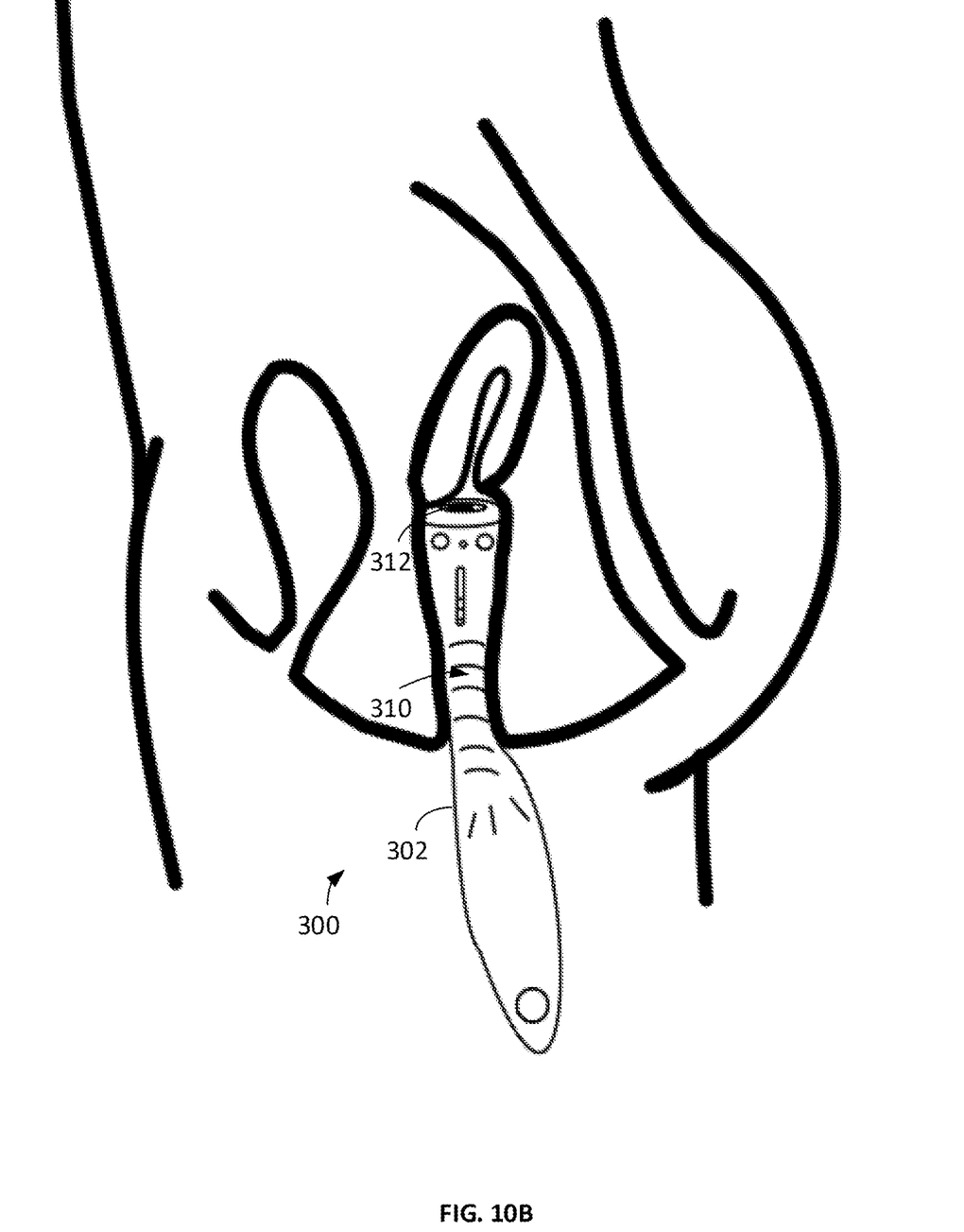
FIG. 10B is a schematic view of the fluid collection device of FIG. 10A inserted within a vagina.

Referring now to FIGS. 10A-10B, a vaginal fluid collection device 300 is illustrated according to various arrangements. The vaginal fluid collection device 300 is similar to the vaginal fluid collection device 100 as described herein. For instance, the vaginal fluid collection device 300 includes an outer membrane 302, similar to the outer the outer membrane of the device 100. Further, an upper section includes a first opening 312, similar to the first opening 112. In addition, the vaginal fluid collection device 300 includes a grooved portion 310. The grooved portion 310 may be positioned in a middle section of the device 300. The grooved portion 310 may include finger-sized grooves (e.g., divots, dips, channels, etc.) to facilitate a better grip for the user. The grooves mimic finger placement for better positioning. FIGS. 10A-10B further illustrates the device 300 in use and compatible with both a normal uterus (FIG. 10A) and a tilted uterus (FIG. 10B).

What is claimed is:

1. A device comprising:
   a collector comprising:
      an upper portion with a opening at an upper end of the upper portion, the upper portion comprising at least one pocket;
      a bottom portion;
   a membrane configured to surround at least a portion of the collector, wherein the membrane comprises:
      an upper section having a portion configured to cover the opening of the collector;
      a lower section connected to the upper portion of the membrane, the lower section having a portion defining a space to store collected fluid;
   wherein when at least a portion of the device is inserted into a vagina of a body, at least a portion of the portion defining the space extends outside the body.

2. The device of claim 1, wherein the upper portion of the collector comprises a protruding circumferential lip at the opening.

3. The device of claim 1, wherein the collector is formed from a silicone material.

4. The device of claim 1, wherein the collector comprises a lower portion comprising a hollow tube having a second opening and a rim.

5. The device of claim 1, wherein the upper portion further comprises a lip configured to form a seal with a wall of a vaginal canal of the vagina of a body.

6. The device of claim 1, wherein the opening has a diameter in a range from 5 mm to 45 mm.

7. The device of claim 4, wherein the collector further comprises a first tapered portion disposed between the upper portion and the lower portion.

8. The device of claim 1, wherein at least a portion of the upper portion of the collector is configured to fit within the membrane.

9. The device of claim 8, wherein the membrane further comprises a second tapered portion disposed between the upper section of the membrane and the lower section of the membrane, wherein the second tapered portion corresponds to the first tapered portion in shape and encloses at least a portion of a first tapered portion disposed between the upper portion and the lower portion.

10. The device of claim 1, wherein the membrane comprises a rim configured to support one or more flaps.

11. The device of claim 1, wherein the membrane comprises one or more hemispherical indentations in the upper section configured to form suction when the collection device is inserted into the vagina.

12. The device of claim 1, wherein the membrane further comprises a transparent panel disposed on the upper section and configured to allow visibility of the collected fluids.

13. The device of claim 1, wherein
   the collector comprises a first tapered portion disposed between the upper portion and the lower portion;
   the membrane comprises a second tapered portion disposed between the upper section of the membrane and the lower section of the membrane; and
   at least one grip indentation disposed on the first and second tapered portions.

14. The device of claim 1, further comprising a removal mechanism, the removal mechanism being at least one of a ring, a handle, a tab, a string, and a hole.

15. The device of claim 1, wherein the upper section and the lower section of the membrane are continuous.

16. The device of claim 1, wherein the at least one pocket is configured to receive a suppository.

17. The device of claim 1, wherein the at least one pocket is disposed on an edge of an inner collector of the upper portion of the collector.

18. The device of claim 1, wherein the at least one pocket comprises a plurality of pockets surrounding at least one flexible flap.

19. The device of claim 11, wherein the at least one pocket comprises a plurality of pockets surrounding the opening.

20. A method, comprising:
   providing a collector, comprising:
      an upper portion with a opening at an upper end of the upper portion, the upper portion comprising at least one pocket;
      a bottom portion;
   providing a membrane, wherein the membrane is configured to surround at least a portion of the collector, wherein the membrane comprises:
   an upper section having a portion configured to cover the opening of the collector;
   a lower section connected to the upper portion of the membrane, the lower section having a portion defining a space to store collected fluid;
   wherein when at least a portion of the device is inserted into a vagina of a body, at least a portion of the portion defining the space extends outside the body.

* * * * *